United States Patent [19]

Kahn

[11] 4,393,878

[45] Jul. 19, 1983

[54] PRESSURE MONITORING METHOD AND APPARATUS

[75] Inventor: Alan R. Kahn, Madison, Wis.

[73] Assignee: Meadox Instruments, Inc., Oakland, N.J.

[21] Appl. No.: 262,381

[22] Filed: May 11, 1981

Related U.S. Application Data

[63] Continuation-in-part of Ser. No. 211,084, Nov. 28, 1980, abandoned.

[51] Int. Cl.³ .............................................. A61B 5/00
[52] U.S. Cl. ..................................... 128/748; 73/715
[58] Field of Search ............... 128/748, 672, 673, 675, 128/687–690; 73/715, 729

[56] References Cited

U.S. PATENT DOCUMENTS

| | | | |
|---|---|---|---|
| 2,831,478 | 4/1958 | Uddenberg et al. ................ | 128/748 |
| 3,099,262 | 7/1963 | Bigliano ............................. | 128/672 |
| 3,299,882 | 1/1967 | Masino ........................... | 128/687 X |
| 3,811,429 | 5/1974 | Fletcher ............................. | 128/687 |
| 3,818,765 | 6/1974 | Eriksen ............................. | 128/675 |
| 3,831,588 | 8/1974 | Rinder ............................. | 128/675 |
| 4,003,141 | 1/1977 | Le Roy ............................. | 128/748 |
| 4,147,161 | 4/1979 | Ikebe et al. ......................... | 128/748 |
| 4,185,641 | 1/1980 | Minior et al. ...................... | 128/748 |
| 4,206,761 | 6/1980 | Cosman ............................. | 128/748 |
| 4,206,762 | 6/1980 | Cosman ............................. | 128/748 |

FOREIGN PATENT DOCUMENTS 1355138  5/1974  United Kingdom .................. 73/715

OTHER PUBLICATIONS

Levin, A. B. "The Use of a Fiberoptic Intracranial Pressure Monitor in Clinical Practice", Neurosurgery, vol. 1, No. 3, Nov./Dec. 1977, pp. 266–271.

Brochure by Ladd Research Industries, Inc., "Intracranial Pressure Monitor for Continuous Measurement of ICP".

Primary Examiner—Lee S. Cohen
Attorney, Agent, or Firm—Isaksen, Lathrop, Esch, Hart & Clark

[57] ABSTRACT

An apparatus (10) which measures and monitors the pressure within a human body includes a pressure sensor (11) having a housing (30) closed by a pressure sensitive diaphragm (34) to define a plenum (35), an exhaust tube (36) mounted within the plenum (35) which terminates adjacent the inner surface of the diaphragm (34), and tubes (13, 15) which transmit a substantially constant flow of gas into the plenum and which withdraw gas from the exhaust tube (36) to a location remote from the body. Changes in pressure within the body cause the diaphragm (34) to alternately close and open the end of the exhaust tube (36), thereby resulting in an increase or decrease in the pressure within the plenum until an equilibrium pressure is reached. A source (12) of gas pressure is provided, as well as a means for providing a substantially uniform flow rate (R) and means for measuring the pressure (14) within the tube (13) that transmits the gas flow to the sensor (11). The flow rates to and from the sensor (11) are compared, and the flow of gas to the sensor (11) is cut off if the flow rates are unequal, a condition indicative of a leak in the sensor (11) or in the tubing (13, 15, 17) that transmits the gas to and from the sensor.

15 Claims, 5 Drawing Figures

PRESSURE MONITORING METHOD AND APPARATUS

This application is a continuation-in-part of prior application Ser. No. 211,084, filed Nov. 28, 1980, now abandoned.

The present invention generally relates to a method and apparatus for monitoring pressure. More particularly, it relates to an apparatus for monitoring pressure inside the body organs and the body cavities of human patients and human and animal subjects.

BACKGROUND OF THE INVENTION

The need to monitor and measure gas and liquid pressures has led to the development of a variety of pressure transducing methods. The monitoring and measuring of pressures at remote or inaccessible sites is usually accomplished by one of the two following methods:

(1) The pressure is transmitted through a pipe or tube to a centrally placed transducer or gauge, or (2) A remote transducer probe is employed which sends a converted signal to a central recording instrument.

The use of the first method requires a fluid connection to the pressure medium being measured. This is not desirable when the fluid column can cause the escape of noxious chemicals, be an avenue for infectious agents, or be a site for obstruction by objects, blood clots, or other protein materials.

The use of the second method which employs a remote transducer probe is also not without disadvantages. The most commonly used remote transducer probes are usually mechanical to electrical transducers which convert the movement of a surface or diaphragm into an electrical signal. Such transducers when reduced to the sizes of 5 mm. or less exhibit too much baseline drift and temperature instability to make accurate measurements at small pressure changes (1 mm Hg) over long periods of time, such as weeks.

There is a special need for a simple, inexpensive, compact, and accurate apparatus which is suitable for monitoring pressures within the body of living animals for clinical and medical research purposes; e.g., the measuring of intracranial pressure.

SUMMARY OF THE PRESENT INVENTION

It is an object of the present invention to disclose a novel pressure monitoring and measuring apparatus and method.

It is a further object to provide an apparatus and method for monitoring and measuring pressures at remote sites.

It is a still further object to provide a simple, inexpensive, compact and accurate apparatus for monitoring pressures inside the bodies of human and animal patients and subjects.

It is another object of the invention to provide an apparatus and method enabling the monitoring and measuring of pressure in remote and small spaces which maintains an accuracy of at least 1 mm Hg for prolonged periods.

The apparatus of the present invention includes a pressure source which supplies fluid under pressure; a pressure sensor including a cup-shaped housing, having an inlet, an outlet, a pressure sensitive diaphragm closing the mouth of the housing to form a plenum and an exhaust tube having one end connected to the outlet and the other end extending into the plenum and terminating adjacent the underside of the pressure sensitive diaphragm; tubing connecting the pressure source to the inlet of the pressure sensor; means insuring a uniform fluid flow; and means for measuring the pressure in the plenum.

In the preferred practice of the present invention, the pressure source supplies a fluid, preferably a gas, at a pressure which is at least twice the maximum pressure to be measured and the means insuring a uniform flow is a restriction which impedes the fluid flow sufficiently to provide a relatively uniform, constant flow. The impedance of the restriction significantly exceeds the combined impedances of the inlet and the exhaust tube so that the pressure drop in the inlet is negligibly small. The measuring means which can be a gauge or a transducer remotely reads the pressure in the plenum of the pressure sensor.

When the pressure outside the diaphragm of the pressure sensor exceeds the pressure inside the plenum, the diaphragm is pressed against the opening of the exhaust tube and blocks the outflow of fluid. The fluid continues to flow through the inlet and increases the pressure in the plenum until it slightly exceeds the pressure outside sensed by the diaphragm. The diaphragm then moves outwardly to unblock the exhaust tube which causes a drop in the pressure in the plenum until it equals the outside pressure. The impedance of the exhaust tube is less than that of the restriction which allows the pressure in the plenum to decrease. The described cycle repeats and by repeating maintains the pressure in the plenum of the pressure sensor very close to the pressure sensed by the diaphragm.

The pressure in the plenum is read by the remote pressure measuring means with only a slight error due to the pressure drop in the inlet tube. This error is rendered insignificantly small by increasing the impedance of the restriction so as to allow only very slow fluid flows. By adjusting the resistance created by the restriction, it is also possible to adjust the rate of filling when the external pressure increases, thereby affecting the response time of the pressure measuring means.

The effective internal surface area of the diaphragm and its external surface area which is in contact with or senses outside pressure are approximately equal because the exhaust tube outlet preferably contacts no more than 30% of the internal surface of the diaphragm at any time.

The apparatus and method of the present invention provide for an inexpensive, accurate measuring and monitoring of pressure and are particularly useful in monitoring pressure in a variety of medical applications including intracranial, intrathoracic, intracardiac, gastrointestinal, intravesicular, (urinary bladder) and similar pressures.

In addition to the above mentioned objects, other objects and advantages of the present invention will be apparent to those skilled in the art from the description which follows.

PREFERRED EMBODIMENT OF THE INVENTION

Figure 1:
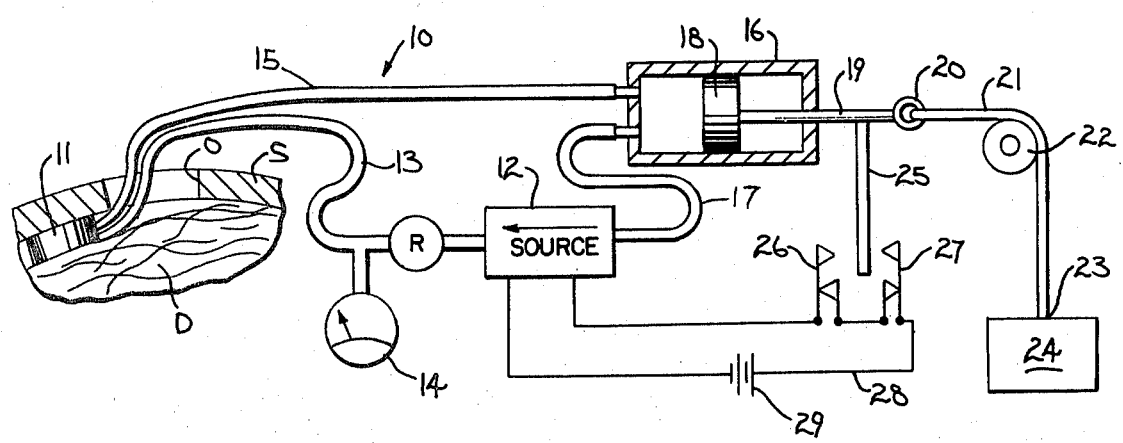
FIG. 1 is a schematic view of one embodiment of the apparatus of the present invention implanted in the brain of a living human to monitor intracranial pressure.

In FIG. 1, is shown an embodiment of the pressure monitoring apparatus of the present invention particularly adapted for measuring intracranial pressure. As seen therein the apparatus, which is generally referred to as 10, includes a pressure sensor 11, a fluid pressure source 12, which is preferably a pump, and tubing 13 which connects the sensor 11 to the pressure source 12. Located intermediate the length of the tubing 13 between the sensor 11 and the pressure source 12 is a pressure measuring means 14 which can be a gauge or an electrical transducer. Positioned along the tubing 13 between the pressure measuring device 14 and the pressure source 12 is a restriction R or other means of insuring uniform flow such as a tubing clamp or a valve. The restriction R provides an impedance to the flow of fluid from the fluid pressure source 12 to the pressure sensor 11 thus providing a relatively constant fluid flow. A second length of tubing 15 can be seen in FIG. 1 leading from the pressure sensor 11 to a sealed variable volume vessel 16 which can be of the piston-type shown or a bellows or the like. The vessel 16 is operatively connected to the pressure source 12 by a third length of tubing 17.

As seen in FIG. 1, the piston 18 of the sealed variable volume vessel 16 has a rod 19 which is connected at its free end 20 to a cord 21 which passes over a pulley 22 and is connected at its free end 23 to a weight 24. Positioned intermediate the length of the rod 19 is a finger 25. The finger 25 extends between two make and break switches 26 and 27 which are located in an electrical circuit 28 which connects the pressure source 12 air pump to an electrical source 29. As seen in the drawing the switches 26 and 27 are both closed.

As seen in FIG. 1, the pressure sensor 11 is implanted in the brain of a human between the dura D and the skull S so that it can measure and monitor intracranial pressure. The tubing 13 and the tubing 15 lead from the pressure sensor 11 through an opening O in the skull S to the outside.

Figure 2:
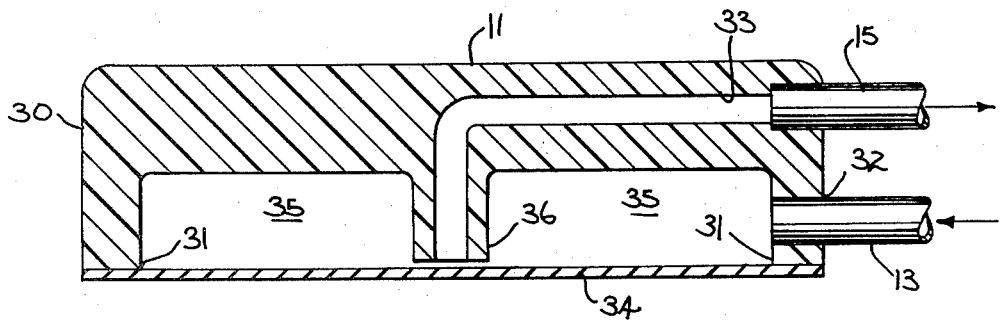
FIG. 2 is an enlarged side elevational view, partly in section, of the pressure sensor seen in FIG. 1.
Figure 3:
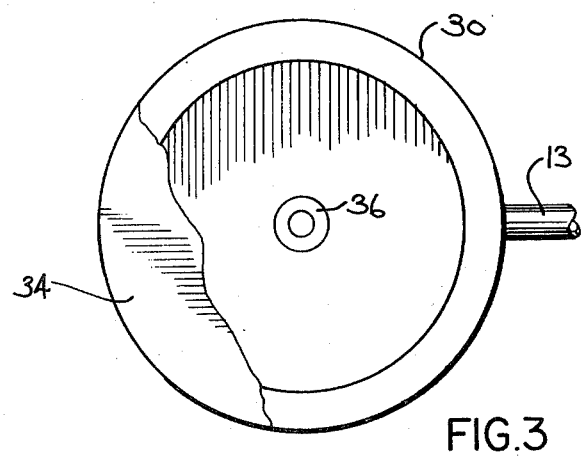
FIG. 3 is a bottom view of the pressure sensor of FIG. 2 with a portion thereof broken away for illustration.

Turning now to FIG. 2, it can be seen that the pressure sensor 11 includes a cup-shaped housing 30 having an open mouth 31, an inlet 32 and an outlet 33. The open mouth 31 of the housing 30 is closed by a flexible, inelastic diaphragm 34 to form a plenum 35. The diaphragm 34 is preferably permanently glued in place. The outlet 33 communicates at one end with the tubing 15 and at the other with an exhaust tube 36 which extends into the plenum 35 of the sensor 11 and terminates just short of the underside of the diaphragm 34. The exact distance between the end of the exhaust tube 36 and the underside of the diaphragm 34 will depend upon the inelasticity and flexibility of the diaphragm, the pressure being measured and the desired sensitivity of the sensor. As seen only in FIG. 3, the exhaust tube 36 is centrally located within the plenum 35.

The embodiment shown in the drawing is particularly adapted for use in measuring pressure in medical applications where the rupture of the diaphragm of the indwelling sensor could allow fluid or air to escape into the body and where the described range of measurement includes negative pressures.

The connection of tubing 15 and the tubing 17 to the chamber of the variable volume vessel 16 provides a closed fluid system which limits the quantity of fluid which can be introduced through a leak in the indwelling sensor 11. Further, the suction force applied to the vessel 16 by the cord 21, pulley 22 and weight 24 maintains a negative pressure in the vessel 16. This provides a stable negative pressure reference which enables the measurement of negative pressure. The negative pressure in the vessel also minimizes the likelihood of air leakage outwards in the event of rupture of the diaphragm 34. It will be appreciated that other means of providing the negative pressure may be used, e.g., the cord 21, pulley 22 and weight 24 could be replaced by a spring.

An additional safety feature of the embodiment illustrated is provided by the combination of the finger 25 and the switches 26 and 27 of the electrical circuit 28. The movement of the piston 18 beyond prescribed limits which might occur due to leaks anywhere in the system will cause the finger 25 to open a switch 26 or 27, turn off the fluid pressure source 12 and alert the operator.

When intended for medical applications, all exposed portions of the pressure sensor 11 and the tubing 13 and 15 are made of a biocompatible plastic material such as silicone elastomer or polyurethane.

In a preferred embodiment for medical use, the housing 30 is molded of a suitable plastic material and is about 1 centimeter in diameter and about 2.5 mms deep. The diaphragm 34 is fabricated of a flexible but inelastic biocompatible plastic about 0.25 mm thick and the exhaust tube 36 extends to within 0.10 mms of the underside of the diaphragm 34. The material, thickness and inelasticity of the diaphragm to be used will depend, or course, upon the intended use of the apparatus and the pressure to be measured.

To verify the accuracy of the miniaturized embodiment of the apparatus 10, a pressure sensor 11, similar to that described above, was implanted in a dog's brain along with a conventional mechanical to electrical transducer in a manner similar to that illustrated in FIG. 1. In order to insure uniform flow the value of the resistance was set using a tubing screw clamp so that the time (70% response) was less than 0.3 seconds. (The base line error was about 0.5 mms Hg.) The pressure source, a tank of oxygen, was set to deliver oxygen at 500 mms Hg. The dog was then subjected to manuevers which altered its intracranial pressure and the pressure measurements were made. The experimental results revealed that the apparatus of the present invention yielded the same results as the conventional unit during steady states and slow changes. Moreover, the apparatus of the present invention was superior in that it tracked fast changes during the injection of saline into the vertricles of the brain while the conventional transducer unit was unable to record such fast changes. Oscillographic traces were used to verify the results.

Further experimentation revealed that the apparatus was accurate up to 200 mms of Hg and that the base line drift over four weeks did not show any change of pressure exceeding 0.2 mm Hg.

It will be apparent to those skilled in the art that although the pressure monitoring apparatus and method of the present invention have been described primarily in connection with the measuring of intracranial pressure, the invention is not so limited. The invention may be used in a variety of medical applications including intracardiac, gastrointestinal, intravesicular, and other applications where a simple, inexpensive, compact and accurate means to measure and monitor pressure can be used to advantage.

In non-medical applications satisfactory results may be obtainable with an apparatus that does not include the variable pressure vessel 16, the cord 21, the pulley 22, the weight 24 and the electrical circuit 28. Such an apparatus might comprise the sensor 11, the pressure source 12, the tubing 13, the resistance R, the pressure measuring means 14 and the tubing 15 with all the named components connected as shown in FIG. 1 except that the tubing 15 would exhaust to the outside.

Figure 4:
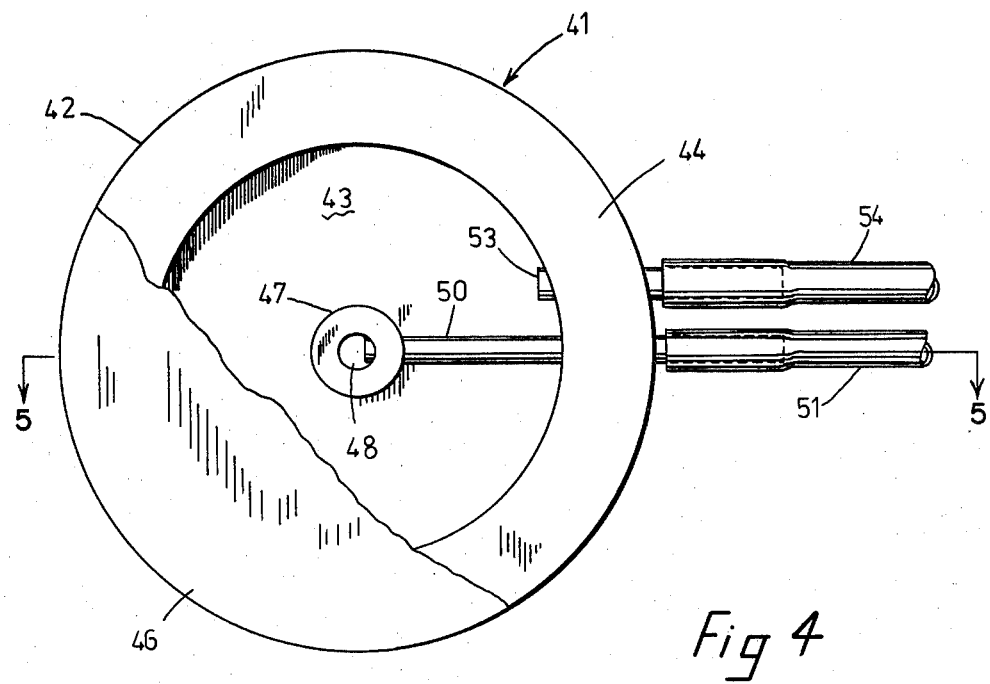
FIG. 4 is a bottom view of an alternative embodiment of a pressure sensor, with a portion thereof broken away for illustration.
Figure 5:
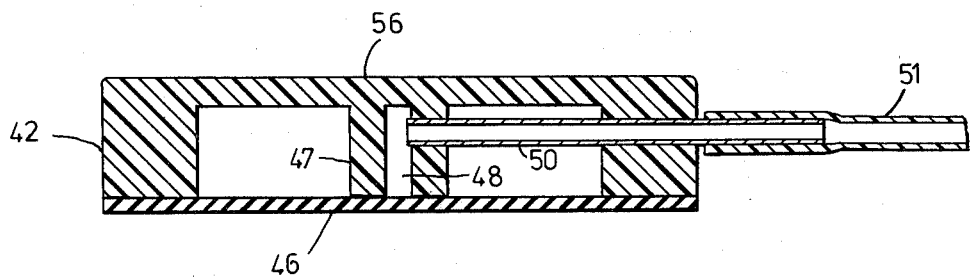
FIG. 5 is a cross-sectional view of the pressure sensor of FIG. 4 taken along the lines 5—5 of FIG. 4.

An alternative embodiment for a pressure sensor capable of being used in the apparatus 10 is shown generally at 41 in FIG. 4. The pressure sensor 41 also includes a cup-shaped housing 42 formed as a circular disc of plastic having a circular open mouth 43 formed in one surface thereof surrounded by a peripheral annular face 44. A flexible diaphragm 46 is secured by glue or other adhesive or by sonic welding, as desired, to the peripheral face 44 of the housing. A portion of the diaphragm 46 is shown broken away in FIG. 4 to illustrate the structure of the pressure sensor under the diaphragm. This structure includes a circular exhaust tube 47 centrally mounted in the mouth 43 and terminating—at a position adjacent the inner side of the diaphragm 46—in an annular face which surrounds the open bore 48 of the exhaust tube. As shown in FIG. 5, the annular face of the exhaust tube is formed substantially coplanar with the peripheral face 44 of the housing. A thin-walled metal outlet pipe 50 has its inner bore in communication with the bore 48 of the exhaust tube and extends outwardly through the outer wall of the housing 42 and is connected to plastic tubing 51 corresponding to the tube 15 shown in FIG. 1. An inlet pipe 53, also formed of a thin-walled metal pipe, extends through the outer wall of the housing 42 such that its bore is in communication with the plenum 43, with the outer end of the inlet pipe 53 being connected to plastic tubing 54 corresponding to the tubing 13 shown in FIG. 1. The outlet pipe 50 and the inlet pipe 53 are preferably mounted closely adjacent to one another at approximately the same elevation in the outer wall of the housing 42 to minimize the space taken up by the pipes and by the tubing connected to them.

As best shown in FIG. 5, the outlet pipe 50 passes through the plenum 43 and the wall of the exhaust tube 47 to the bore 48 of the exhaust tube. This outlet arrangement may be compared to the outlet 33 formed as a channel in the housing 30, as shown in FIG. 2. The pressure sensor structure of FIGS. 4 and 5 has the advantage over the structure shown in FIGS. 2 and 3 of having a thinner top wall portion 56 of the sensor housing since the outlet for the sensor 41 does not have to be formed as a channel through the housing. As is illustrated in FIG. 5, the top wall 56 of the sensor 41 need only be thick enough to provide structural strength and integrity. For example, the height of the pressure sensor 41, i.e., the distance from the outer surface of the diaphragm 46 to the surface of the top wall 56 of the housing, may be in the range of 1.5 mm., to thereby minimize the space within the patient that is occupied by the sensor. The sensor structure 41 also has the advantage of allowing the plastic tubes 51 and 54 to extend from the sensor in closely spaced, parallel relation. The inlet and outlet pipes 53 and 50 are preferably located at a position in the wall of the sensor housing above the bottom of the mouth of the housing such that the top wall of the sensor housing can be made as thin as desired.

The housing of the pressure sensor 41 is formed of similar materials to the pressure sensor 11: biocompatible plastic materials such as silicone or polyurethane; and similar materials are used for the diaphragm 46 and the tubing 51 and 54. A stiffer diaphragm (less elastic) may be provided, if desired, by molding a nylon mesh within the material of the diaphragm.

Those skilled in the art will appreciate that the novel mechanical design of the pressure sensor of the present invention provides an inherent and automatic servo-control. The sensor with its diaphragm which alternately opens and closes the exhaust tube automatically maintains the pressure on the plenum side of the diaphragm nearly equal to the pressure outside in the medium being tested and provides a simple, inexpensive and reliable means for measuring and monitoring pressure.

It will be readily apparent to those skilled in the art that a number of changes and modifications can be made without departing from the spirit of the present invention. For example, although the diaphragm is shown as glued in place closing the mouth of the sensor housing, it might be more advantageous in some applications to removably affix the diaphragm to the housing by using a retaining collar or similar means. Therefore, it is intended that the invention not be limited by any of the foregoing description but only by the claims which follow.

What is claimed is:

1. Pressure monitoring apparatus comprising:
   (a) a fluid pressure pump supplying gas under pressure;
   (b) a pressure sensor including:
      (1) a cup shaped housing having an open mouth and having an inlet and an outlet formed therein;
      (2) a flexible diaphragm sealed over the open mouth of the housing to define a plenum between the walls of the mouth in the housing and the diaphragm, and wherein the inlet formed in the housing is in communication with the plenum;
      (3) an exhaust tube centrally mounted in the housing within the plenum with an end thereof terminating adjacent the inner side of the diaphragm and connected to be in communication with the outlet from the housing;
   (c) tubing connecting the pump to the inlet in the sensor housing to supply gas under pressure to the inlet and also connecting the outlet in the sensor housing to the pump to form a closed system;
   (d) a flow restriction connected in the tubing between the pump and the inlet to the sensor housing so that the flow to the sensor is substantially uniform; and
   (e) means for measuring pressure connected to measure the pressure in the tubing between the flow restriction and the inlet to the sensor housing, whereby changes in ambient pressure at the pressure sensor will result in movement of the diaphragm to alternately open and close the exhaust tube to automatically maintain the pressure within the plenum approximately equal to the ambient pressure, and whereby the means for measuring pressure in the tubing will measure a pressure which is approximately equal to the pressure within the plenum.

2. The pressure monitoring apparatus of claim 1 in which the pressure pump supplies gas at a pressure at least twice the maximum pressure to be measured by the means for measuring pressure.

3. The pressure monitoring apparatus of claim 1 including means connected to the tubing returning gas from the sensor to the pump for providing a stable negative pressure reference in the tubing which enables the measurement of negative pressure at the pressure sensor.

4. The pressure monitoring apparatus of claim 1 including a sealed vessel connected in the tubing between the outlet of the sensor housing and the pump and means for maintaining a negative pressure in the sealed vessel, whereby negative ambient pressures can be sensed by the pressure sensor and whereby, if a leak develops in the pressure sensor, the gas supplied to the sensor will tend to be withdrawn into the vessel rather than leaking out of the sensor.

5. The pressure monitoring apparatus of claim 4 wherein the means for maintaining a negative pressure in the sealed vessel includes a piston slideably engaging the walls of the vessel in substantially pressure tight relationship and a weight operatively connected to the piston to provide a constant force pulling on the piston to tend to draw the piston in a direction to enlarge the internal volume of the sealed vessel.

6. The pressure monitoring apparatus of claim 5 including a pair of electrical switches connected in an electrical circuit supplying electrical power to drive the pump, means connected to the piston and responsive to movement of the piston beyond preselected limits of either increased or decreased volume of the sealed vessel for opening one or the other of the switches to cut-off electrical power to the pump and thereby shut off the flow of gas to the pressure sensor, whereby the pressure monitoring apparatus will automatically shut down if a leak of gas supplied to or withdrawn from the sensor occurs.

7. The pressure monitoring apparatus of claim 1 wherein the housing of the pressure sensor is formed of plastic having a circular open mouth formed therein to define a cup-shape, the exhaust tube is formed integrally with the housing and extends upwardly from the bottom surface of the mouth of the housing at the center thereof and has a surface area adjacent the diaphragm which is not more than 30% of the area of the mouth of the housing covered by the diaphragm, and wherein the outlet in the housing includes a channel formed in the housing extending from the end of the exhaust tube adjacent the diaphragm and to the surface of the housing for connection to the tubing connected to the pump, and wherein the inlet is formed as a hole in the wall of the housing which terminates in the plenum and which is connected to the tubing leading from the pump, and wherein the points of connection of the tubing to the inlet and the outlet are adjacent to one another.

8. The pressure monitoring apparatus of claim 1 wherein the pressure sensor housing is formed as a circular plastic disc having a circular open mouth formed in one surface of the housing which is surrounded by a peripheral annular face and leaving a top wall at the other surface of the disc, and wherein the diaphragm is sealed to the surface of the peripheral annular face to cover the mouth of the housing and define the plenum between the diaphragm and the interior walls of the mouth of the housing, wherein the exhaust tube is formed integrally with the housing, extends from the center of the top wall of the housing to terminate at a position adjacent the inner side of the diaphragm, and has a circular bore therein, and wherein an outlet pipe formed of metal extends through the wall of the exhaust tube into communication with the bore within the exhaust tube and also extends through the walls of the housing to the outside thereof to define the outlet from the housing and is connected to the tubing leading to the pressure pump, and wherein the inlet includes an inlet pipe formed of metal extending through the wall of the housing from a position outside of the housing into the plenum within the housing, the piston of the inlet pipe outside of the housing being connected to the tubing leading from the pressure pump, the inlet and outlet pipes being mounted closely adjacent to one another to minimize the space taken up by the pipes and by the tubing connected to them, and the inlet and outlet pipes being located at a position in the wall of the sensor being between the diaphragm and the top wall of the housing such that the thickness of the top wall of the housing can be minimized.

9. The pressure monitoring apparatus of claim 7 or 8 wherein the pressure sensor housing is formed of a material selected from the group consisting of silicone and polyurethane.

10. The pressure sensor of claim 8 wherein the height of the sensor from the surface of the diaphragm to the top surface of the housing is approximately 1.5 mm.

11. The pressure sensor of claim 1 wherein the exhaust tube terminates just short of the diaphragm whereby gas can flow from the plenum into the exhaust tube when the pressure on either side of the diaphragm is approximately equal.

12. A pressure sensor adapted for implantation in a human body comprising:
 (a) a cup-shaped housing formed as a circular plastic disc having a circular open mouth formed in one surface which is surrounded by a peripheral annular face and leaving a top wall at the other surface of the disc;
 (b) a pressure sensitive diaphragm sealed to the surfaces of the peripheral annular face to close the open mouth of the housing to define a plenum between the diaphragm and the interior walls of the mouth in the housing;
 (c) an exhaust tube formed integrally with the housing and extending from the top wall of the housing within the center of the plenum to terminate at a position adjacent to the inner side of the diaphragm, the exhaust tube having a circular bore therein;
 (d) an outlet from the housing including an outlet pipe formed of metal extending through the walls of the exhaust tube into communication with the bore within the exhaust tube and also extending through the walls of the housing to the outside thereof where it is adapted to be connected to external tubing;
 (e) an inlet for the housing including an inlet pipe formed of metal extending through the wall of the housing from a position outside the housing into the plenum within the housing, the portion of the inlet pipe outside of the housing being adapted to be connected to external tubing, the inlet and outlet pipes being mounted closely adjacent to one another to minimize the space taken up by the pipes and by the tubing to be connected to them, and the inlet and outlet pipes being located at a position in the wall of the sensor housing between the diaphragm and the top wall of the housing such that the thickness of the top wall of the housing can be minimized.

13. The sensor of claim 12 wherein the pressure sensor housing is formed of a material selected from the group consisting of silicone and polyurethane.

14. A method of measuring the pressure within a human body comprising the steps of:
   (a) implanting within a human body a sensor which includes a housing closed by a diaphragm to define a plenum therein and an exhaust tube in the plenum terminating at an end adjacent the inner surface of the diaphragm;
   (b) providing a first length of tubing which extends from a location outside the human body to the sensor and is in communication with the plenum therein;
   (c) providing a second length of tubing which extends from a location outside the human body to the sensor and is in communication with the exhaust tube therein;
   (d) providing gas through the first tubing at a substantially constant flow rate into the plenum in the housing;
   (e) withdrawing gas through the exhaust tube when the pressure outside the sensor is less than the pressure in the plenum such that the diaphragm is spaced away from the opening to the exhaust tube and transmitting the gas flow through the second tubing, and substantially cutting off the flow of gas into the exhaust tube when the pressure in the plenum is lower than the pressure outside the sensor such that the diaphragm is pressed against the opening of the exhaust tube;
   (f) measuring the pressure in the first tubing which provides the gas flow to the sensor to provide an estimate of the pressure within the plenum of the sensor which is itself substantially equal to the pressure outside the sensor; and
   (g) providing a substantially constant negative pressure to the second tubing which transmits the gas from the pressure sensor thereby to aid the withdrawl of any gas that is introduced into the sensor and reduce the possibility of gas being accidentally injected into the human body if the sensor develops a leak, and to allow the sensor to record negative pressure.

15. The method of claim 14 including the step of comparing the flow of gas into the sensor with the flow of gas from the sensor and cutting off the flow of gas when the flow rates are unequal, which is an indication that a leak has developed in the system.

* * * * *

UNITED STATES PATENT AND TRADEMARK OFFICE
CERTIFICATE OF CORRECTION

PATENT NO. : 4,393,878
DATED : July 19, 1983
INVENTOR(S) : Alan R. Kahn

It is certified that error appears in the above-identified patent and that said Letters Patent are hereby corrected as shown below:

Claim 8, Column 8, line 16, change "piston" to --portion--.

Claim 8, Column 8, line 23, change "being" to --housing--.

Signed and Sealed this

Twentieth Day of September 1983

[SEAL]

Attest:

Attesting Officer

GERALD J. MOSSINGHOFF
Commissioner of Patents and Trademarks